US012089936B2

(12) United States Patent
Cembrowski

(10) Patent No.: US 12,089,936 B2
(45) Date of Patent: *Sep. 17, 2024

(54) METHOD AND APPARATUS FOR INVERSION DETECTION

(71) Applicant: CCQCC Corp., Edmonton (CA)

(72) Inventor: George S. Cembrowski, Edmonton (CA)

(73) Assignee: CCQCC Corp., Edmonton (CA)

( * ) Notice: Subject to any disclaimer, the term of this patent is extended or adjusted under 35 U.S.C. 154(b) by 238 days.

This patent is subject to a terminal disclaimer.

(21) Appl. No.: 17/571,080

(22) Filed: Jan. 7, 2022

(65) Prior Publication Data

US 2022/0202329 A1 Jun. 30, 2022

Related U.S. Application Data

(63) Continuation of application No. 16/280,558, filed on Feb. 20, 2019, now Pat. No. 11,241,178, which is a
(Continued)

(51) Int. Cl.
*A61B 5/15* (2006.01)
*A61B 5/153* (2006.01)
(Continued)

(52) U.S. Cl.
CPC ...... *A61B 5/150809* (2013.01); *A61B 5/1405* (2013.01); *A61B 5/15003* (2013.01);
(Continued)

(58) Field of Classification Search
CPC ........ A61B 5/150755; A61B 5/150763; A61B 5/150786; A61B 5/150809;
(Continued)

(56) References Cited

U.S. PATENT DOCUMENTS 4,910,661 A 3/1990 Barth et al.
6,662,068 B1 12/2003 Ghaffari
(Continued)

OTHER PUBLICATIONS

U.S. Appl. No. 13/800,857 U.S. Pat. No. 9,439,590, filed Mar. 13, 2013, Method and Apparatus for Blood Collection.
(Continued)

*Primary Examiner* — Jill A Warden
*Assistant Examiner* — Dwayne K Handy
(74) *Attorney, Agent, or Firm* — Schwegman Lundberg & Woessner, P.A.

(57) ABSTRACT

A method for inversion counting or phlebotomist monitoring can include identifying, by processing circuitry, whether a blood collection tube is present in image data from a camera situated to capture images of a phlebotomist collecting a sample, in response to identifying the blood collection tube is present in the field of view of the camera based on the image data, identifying whether the blood collection tube includes blood therein, after identifying the blood is present in the blood collection tube, counting, based on the image data, a number of inversions performed on the blood collection tube, and in response to determining the number of inversions performed is less than a required number of inversions, issuing an alert indicating that insufficient inversions were performed.

20 Claims, 8 Drawing Sheets

Related U.S. Application Data continuation-in-part of application No. 16/054,826, filed on Aug. 3, 2018, now abandoned, which is a continuation of application No. 15/240,915, filed on Aug. 18, 2016, now Pat. No. 10,052,054, which is a continuation of application No. 13/800,857, filed on Mar. 13, 2013, now Pat. No. 9,439,590.

(51) Int. Cl.
| | |
|---|---|
| A61B 5/157 | (2006.01) |
| A61M 1/36 | (2006.01) |
| B01L 3/00 | (2006.01) |
| G01N 33/49 | (2006.01) |

(52) U.S. Cl.
CPC .. *A61B 5/150351* (2013.01); *A61B 5/150755* (2013.01); *A61B 5/150786* (2013.01); *A61B 5/15087* (2013.01); *A61B 5/153* (2013.01); *A61B 5/157* (2013.01); *A61M 1/3633* (2013.01); *B01L 3/5082* (2013.01); *B01L 2300/021* (2013.01); *B01L 2300/042* (2013.01); *B01L 2300/0663* (2013.01); *G01N 33/49* (2013.01)

(58) Field of Classification Search
CPC .......... A61B 5/150824; A61M 1/0204; A61M 1/025; A61M 1/3616; A61M 2209/01; B01L 3/5082; B25J 9/1697; B28C 7/028; G06K 9/00201

See application file for complete search history.

(56) References Cited

U.S. PATENT DOCUMENTS

| | | | |
|---|---|---|---|
| 8,761,922 B2 | 6/2014 | Dekar | |
| 9,439,590 B2 | 9/2016 | Cembrowski | |
| 9,716,757 B2 | 7/2017 | Fernandes | |
| 10,052,054 B2 | 8/2018 | Cembrowski | |
| 11,241,178 B2 * | 2/2022 | Cembrowski | A61B 5/157 |
| 2003/0031357 A1 | 2/2003 | Wenzel et al. | |
| 2007/0106419 A1 | 5/2007 | Rachamadugu | |
| 2007/0293983 A1 | 12/2007 | Butler | |
| 2010/0032437 A1 | 2/2010 | Lossau | |
| 2011/0313684 A1 | 12/2011 | Furrer et al. | |
| 2014/0121845 A1 | 5/2014 | Mueller | |
| 2014/0261872 A1 | 9/2014 | Cembrowski | |
| 2015/0290795 A1 | 10/2015 | Oleynik | |
| 2017/0035338 A1 | 2/2017 | Cembrowski | |
| 2017/0300753 A1 | 10/2017 | Billi et al. | |
| 2019/0167172 A1 | 6/2019 | Cembrowski | |
| 2019/0175089 A1 | 6/2019 | Cembrowski | |

OTHER PUBLICATIONS

U.S. Appl. No. 15/240,915 U.S. Pat. No. 10,052,054, filed Aug. 18, 2016, Method and Apparatus for Blood Collection.

U.S. Appl. No. 16/054,826, filed Aug. 3, 2018, Method and Apparatus for Blood Collection.

U.S. Appl. No. 16/280,558, filed Feb. 20, 2019, Method and Apparatus for Inversion Detection.

U.S. Appl. No. 13/800,857, Final Office Action mailed Jan. 16, 2015, 6 pgs.

U.S. Appl. No. 13/800,857, Final Office Action mailed Feb. 2, 2016, 7 pgs.

U.S. Appl. No. 13/800,857, Non Final Office Action mailed Jun. 18, 2014, 6 pgs.

U.S. Appl. No. 13/800,857, Non Final Office Action mailed Jul. 10, 2015, 9 pgs.

U.S. Appl. No. 13/800,857, Notice of Allowance mailed May 12, 2016, 10 pgs.

U.S. Appl. No. 13/800,857, Response filed Mar. 17, 2015 to Final Office Action mailed Jan. 16, 2015, 7 pgs.

U.S. Appl. No. 13/800,857, Response filed Mar. 18, 2016 to Final Office Action mailed Feb. 2, 2016, 6 pgs.

U.S. Appl. No. 13/800,857, Response filed Sep. 17, 2014 to Non Final Office Action mailed Jun. 18, 2014, 7 pgs.

U.S. Appl. No. 13/800,857, Response filed Oct. 12, 2015 to Non Final Office Action mailed Jul. 10, 2015, 7 pgs.

U.S. Appl. No. 15/240,915 Response filed Jan. 5, 2018 to Non-Final Office Action mailed Nov. 3, 2017, 6 pgs.

U.S. Appl. No. 15/240,915, Non Final Office Action mailed Nov. 3, 2017, 6 pgs.

U.S. Appl. No. 15/240,915, Notice of Allowance mailed Apr. 18, 2018, 7 pgs.

U.S. Appl. No. 15/240,915, Preliminary Amendment filed Oct. 25, 2016, 5 pgs.

U.S. Appl. No. 16/054,826, Non Final Office Action mailed Jul. 25, 2019, 7 pgs.

U.S. Appl. No. 16/280,558, Corrected Notice of Allowability mailed Oct. 6, 2021, 3 pgs.

U.S. Appl. No. 16/280,558, Non Final Office Action mailed Jun. 1, 2021, 11 pgs.

U.S. Appl. No. 16/280,558, Notice of Allowance mailed Sep. 29, 2021, 12 pgs.

U.S. Appl. No. 16/280,558, Response filed Aug. 23, 2021 to Non Final Office Action mailed Jun. 1, 2021, 9 pgs.

"BD Vacutainer: Evacuated Blood Collection System", Product Insert, Becton, Dickinson and Company, Franklin Lakes, NJ, [Online] Retrieved from the Internet: <URL; https://www.bd.com/vacutainer/pdfs/VDP40161.pdf>, (2015), 1-5.

* cited by examiner

METHOD AND APPARATUS FOR INVERSION DETECTION

RELATED APPLICATIONS

This application is a continuation of and claims the benefit of priority under 35 U.S.C. § 120 to U.S. patent application Ser. No. 16/280,558, filed on Feb. 20, 2019, which is continuation-in-part of and claims the benefit of priority under 35 U.S.C. § 120 to U.S. patent application Ser. No. 16/054,826, filed on Aug. 3, 2018, which is a continuation of and claims the benefit of priority under 35 U.S.C. § 120 to U.S. patent application Ser. No. 15/240,915, filed on Aug. 18, 2016, which is a continuation of and claims the benefit of priority under 35 U.S.C. § 120 to U.S. patent application Ser. No. 13/800,857, filed on Mar. 13, 2013, each of which is hereby incorporated by reference herein in its entirety.

TECHNICAL FIELD

This technology relates to biological sample collection in general and more particularly to methods and apparatuses for monitoring biological sample collection.

BACKGROUND

Each day, worldwide, hundreds of thousands of patients visit blood collection and other biological sample collection centers, such as for the purpose of getting sampled for eventual or immediate diagnostic testing. During a patient visit, a phlebotomist punctures the patient's superficial vein (usually an arm vein) with a hollow needle and blood is aspirated into evacuated plastic or glass tubes. These plastic or glass tubes usually contain anticoagulants or procoagulants, compounds that are placed as liquid into the blood collection tube or sprayed onto the inside surface of the tube. For these anticoagulants (or procoagulants) to work properly, the fresh incoming blood must be adequately mixed with the anti- or pro-coagulant and there must be a sufficient volume of blood or other biological sample in the container. In the absence of mixing or because of insufficient mixing or insufficient sample volume, the incompletely reacted blood can form clots that can result in the malfunction of the blood analyzer (including plugging) or an incorrect analysis of the blood specimen leading to diagnostic errors and delays in diagnosis. One example of insufficient mixing causing misdiagnosis is falsely elevated troponin (an indicator of myocardial infarction) in plastic blood tubes containing the anticoagulant lithium heparin. Moreover, despite continuingly reminding blood drawing staff to mix their blood tubes after drawing, the inversion step constitutes only one of a great many steps in the typical phlebotomy process, and there are considerable external and internal pressures that hurry the phlebotomist.

BRIEF DESCRIPTION OF IRE DRAWINGS

The accompanying figures, in which like reference numerals refer to identical or functionally-similar elements throughout the separate views and which are incorporated in and form a part of the specification, further illustrate the present technology and, together with the detailed description of the technology, serve to explain the principles of the present technology.

DETAILED DESCRIPTION

Figure 1:
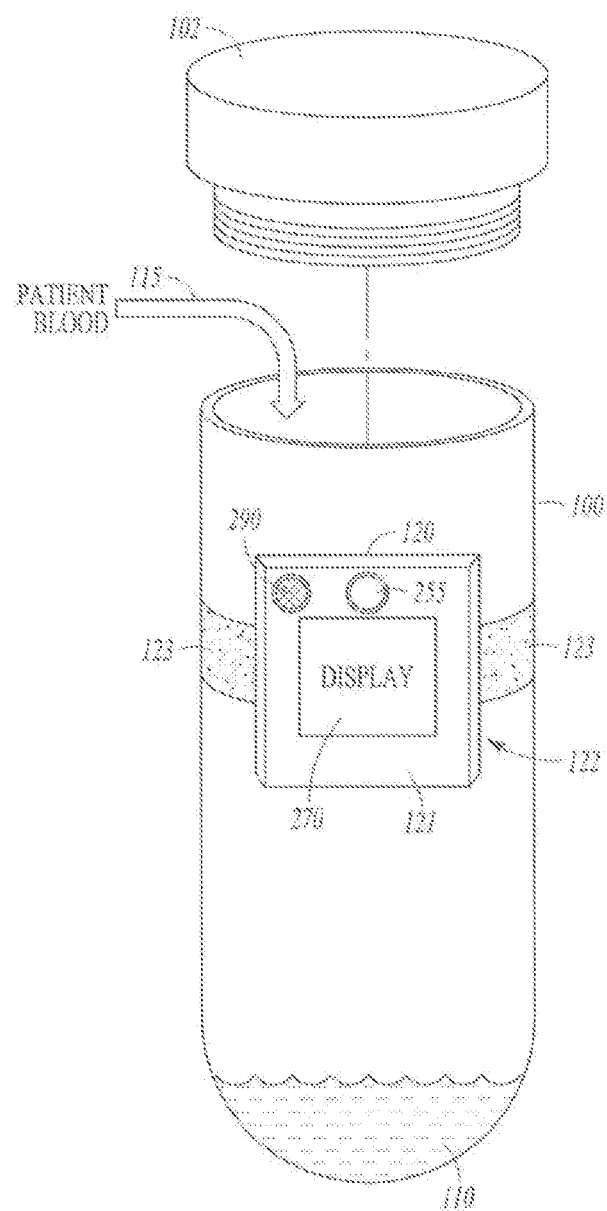
FIGS. 1, 2A, 2B and 3 illustrate blood collection apparatus according to the present technology.
Figure 2A:
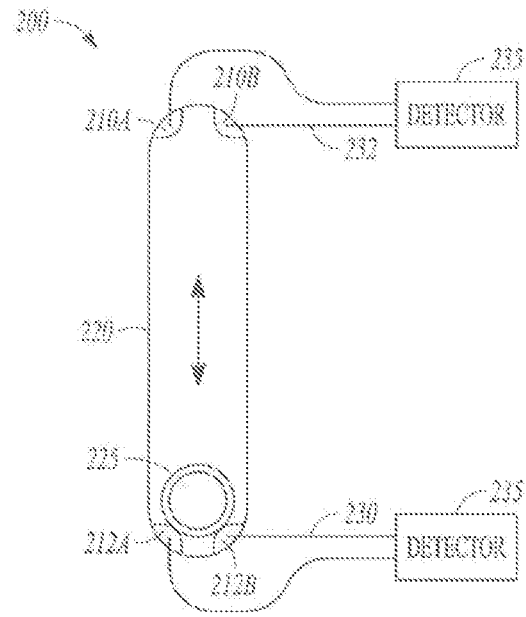
Figure 2B:
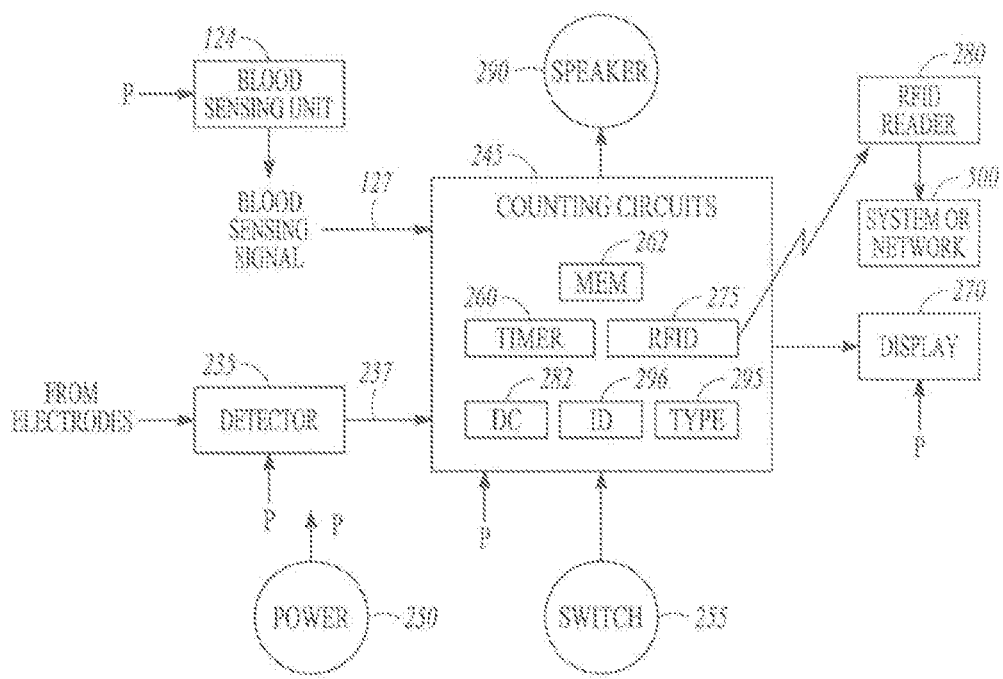

The following description should be read with reference to the drawings, in which like elements in different drawings are numbered in like fashion. The drawings, which are not necessarily to scale, depict selected embodiments and are not intended to limit the scope of the invention. Although examples of systems and methods are illustrated in the various views, those skilled in the art will recognize that many of the examples provided have suitable alternatives that can be utilized Referring now to FIGS. 1, 2A, 2B and 3, there is illustrated various embodiments of method and apparatus for collecting blood or other biological sample. An empty blood drawing container 100, in this example a cylindrical tube, includes anti-coagulant substance 110, and a mix detection unit 120 mounted in a housing 121 and capable of detecting, directly or indirectly, the level of mixing of blood 115 drawn from a patient into the container 100 and anti-coagulant 110. A stopper or other closure element 102 (sometimes called a cap) provides for closing the container 100 once the blood is collected into the container, and before the blood is mixed with the anti-coagulant 110. In one embodiment, blood 115 is drawn from a patient using a needle inserted into a vein or artery.

According to one example embodiment, the mix detection unit 120 comprises an inversion counting device 200 including a pair of contacts 210A, 210B, 212A and 212B, on each end of an enclosure 220. Enclosure 220 may, for example, be tubular in shape. A metallic element 225, such as a metallic ball or slug, is positioned and sized to travel between the opposite ends or sides of enclosure 220, alternately closing a circuit 230 or 232 between the contacts, as the container 100 is inverted. Alternatively, element 225 may be a conductive liquid, such as mercury, or a conductive granular material that can flow between ends or sides of the enclosure 220. The closing of circuit 230 or 232 is detected by electronic circuit closure detector 235 that produces an electronic signal, count or record 237 for each detection of the closing of circuit closure detector 235. Electronic counting circuits 245 counts each electronic signal, or otherwise keeps track of the number of counts detected by detector 235. Counting circuits 245 are connected to, in one embodiment, a display 270 that, under control of count circuits 245, displays a count, which is representative of the number of inversions of the container 100. A power supply 250, such as but not limited to a battery of any suitable type, supplies power P to counting circuits 245. According to one example embodiment, a switch 255 activates counting circuits 245.

Switch 255 may be activated by the medical personnel withdrawing blood from a patient into collection container 100 in order to activate counting circuits 245. Switch 255 may be a mechanical switch, an electrostatic switch, or any other type of switch, but preferably a switch readily activated medical personnel handling the collection container with latex gloves or other sterile hand wear. According to one example embodiment, circuits 245 include a timer 260 that, upon activation of circuits 245, allows circuits 245 to count only those circuit closures occurring within a set period of time from activation, such as one minute, or to determine the time elapsed between each full inversion, so that the rate of inversion may be measured or recorded. The count of circuit closures, in one embodiment, is stored in a memory circuit 262, and can be read out by use of the display 270 or read out by wireless signals, such as by use of an RFID reader 280 and an RFID circuit 275, capable of wirelessly communicating with reader 280, connected directly or indirectly to the memory circuit 262. According to one example embodiment, circuits 245 are implemented using a programmable processing device such as a microprocessor with internal or external memory, and software is used to program the processing device to carry out the functions described herein with respect to circuits 245.

According to another example embodiment, the circuits 245 may be powered at all times and not require a switch, but only count and record the number of contact closures it detects if at least a predetermined number occur with a set period of time. For example, circuits 245 may be configured to only record the number of contact closures if at least at desired number of consecutive opposite end closures are recorded within a specified or desired period of time, such as at least four (4) consecutive closures within six (6) seconds. This would, for example, preclude counting most all instances of inadvertent inversions or jostling or shaking of the blood container 100, while providing a count of intended inversions or movements of the blood container by a blood handling professional for the purposes of mixing drawn blood with the anti-coagulant 110.

According to yet another example embodiment, memory circuit 262 may be used to store a desired or expected count 282 of container inversions, represented in this example embodiment by circuit closures, and counting circuits 245 can further be configured to compare the count of circuit closures to the count 282, and indicate, for example with a message or symbol displayed on display 270, that the count has been reached. Alternatively, circuits 245 may produce a sound to indicate the count has been reached, through an optional speaker element 290. A desired inversion count 282 may be obtained, for example, from the manufacturer of each particular type of blood drawing container. The manufacturer typically enumerates the number of inversions that must be performed for each type of blood drawing tube they distribute.

In still another embodiment, either or both the type 295 of blood collection container, and a unique serial number or identification (ID) 296 for the container, are also stored in the memory circuit 262, for later recall and display on display 270 or electronic output to a reading device or computing apparatus.

According to other example embodiments, the counting apparatus or mechanism may take many other forms, and the blood collection technology described herein is not limited to any particular counting mechanism. For example, the movement of the movable element may be optically detected with an optical sensor in each end of the tube, wherein a light (visible or not visible) beam shone from an optical emitter is received on a corresponding optical light detector and the beam is broken by the presence of the moving element. In the alternative, many other mechanical, optical or other mechanisms may be provided to count inversions or mixing action. In another form, the counting apparatus may be formed from micro-mechanical components. Or, an integrated circuit accelerometer may be provided, wherein counting circuits 245 is configured to receive accelerometer signals and determine the changing orientation of the collection container, and derive a count of inversions or mixing motions therefrom.

According to still another example embodiment, unit 120 includes a blood sensing unit 124 (FIG. 2B), for example employing optical sensing elements, and circuits 245 include an input that is activated by a signal 127 generated by unit 124 when blood flows into the container. Upon detection of blood in the container 100, circuits 245 are activated to count the number of inversions that occur in a set amount of time after detection of the blood. For example, the sensing unit 124 may detect a change in the ambient level of light in the blood collection container due to the receipt of blood into the container. However, any other suitable approach to detecting the presence of blood may also be used. By use of this mechanism, the unit 120 is capable of determining how soon after blood is received in the container 100 that the mixing occurs.

Figure 3:
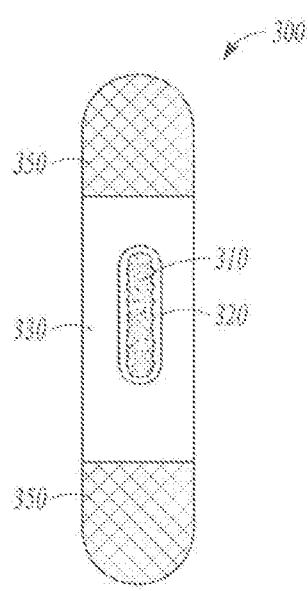

According to still another example embodiment, apparatus 120 may use one or more chemical reactions to detect the level of mixing, such as shown in FIG. 3. As illustrated in FIG. 3, an apparatus 300 may include solution 310 contained inside a breakable capsule 320 inside a flexible walled tube 330. Capsule 320 may be broken by medical personnel by applying pressure on the outside surface of the wall of tube 330 and in turn capsule 320 to break the capsule, which may be formed of thin glass or plastic or other material. Chemical elements or compounds 350 on each end of a tube 330 react with solution 310 released from capsule 320, and in one example embodiment, turn color based on the level of mixing of solution 310 with elements or compounds 350. If elements or compounds 350 on both end of the tube attain the desired color the proper mixing level would be evidenced.

According to still other embodiments of the present technology, the mix detection unit 120 may be operatively coupled or attached to the blood collection container in a variety of different ways. In one example embodiment, unit 120, and more particularly the housing 121 of unit 120, may be mounted outside the collection container, either in a removable fashion or in a permanent fashion, using a fastening mechanism 122. Mechanism 122 may be, for example in one example embodiment, an adhesive that fixes, through adhesive action, the housing 121 to container 100. In another embodiment, mechanism 122 may be a sleeve 123 that wraps around the outside perimeter of container 100, to hold housing 121 in place adjacent container 100. Or, a sleeve 123 may be elastic or inelastic, and provide for elastically encircling the container 100 or providing an interference fit with the container 100. Alternatively, container 100 may include a mechanical or topographical feature on its outside surface to allow mechanism 122 to snap on or clip onto housing 121 in operation, accordingly, housing 121 would be disposed of with container 100 should container 100 be disposed of, or it could be sterilized with container 100 if container 100 were to be reused. Alternatively, housing 121 could be removed from attachment to container 100 and disposed of or sterilized and reset by electronic means for reuse with a new or recycled container 100.

Thus, as described above, there is provided a number of methods for collecting blood, including a method that provides for filling a blood collection container with blood, inverting the blood collection container by hand to mix the blood with an anti-coagulant, and viewing or listening to an indication generated by a mix detection device attached to the blood collection container, wherein the indication provides information about the appropriate amount of mixing for the blood.

According to one example embodiment (FIG. 2B), the count of inversions (or other indication of mixing) is read or transmitted, for example using the above-mentioned RFID mechanism, or any other wireless mechanism such as near-field, Blue Tooth® or other wireless transmissions, to a central device or computing system, or network, optionally along with the serial number of the blood container or type of blood container, as either or both may be optionally stored and read. The blood mixing practices of phlebotomists can thus be continually or intermittently assessed. This count could also be available in the central laboratory where the blood specimens are processed and distributed. Specimens that were not mixed might be pulled of the line and not analyzed. Research could correlate the mixing to deficiencies in laboratory testing. Such research would be useful in developing newer blood containers and tubes. The end product of such a counter would result in improved patient safety, higher efficiency in phlebotomy and total decreased costs to the health care system. Furthermore, having records of mixing compliance would be useful in training new phlebotomists.

Figure 4:
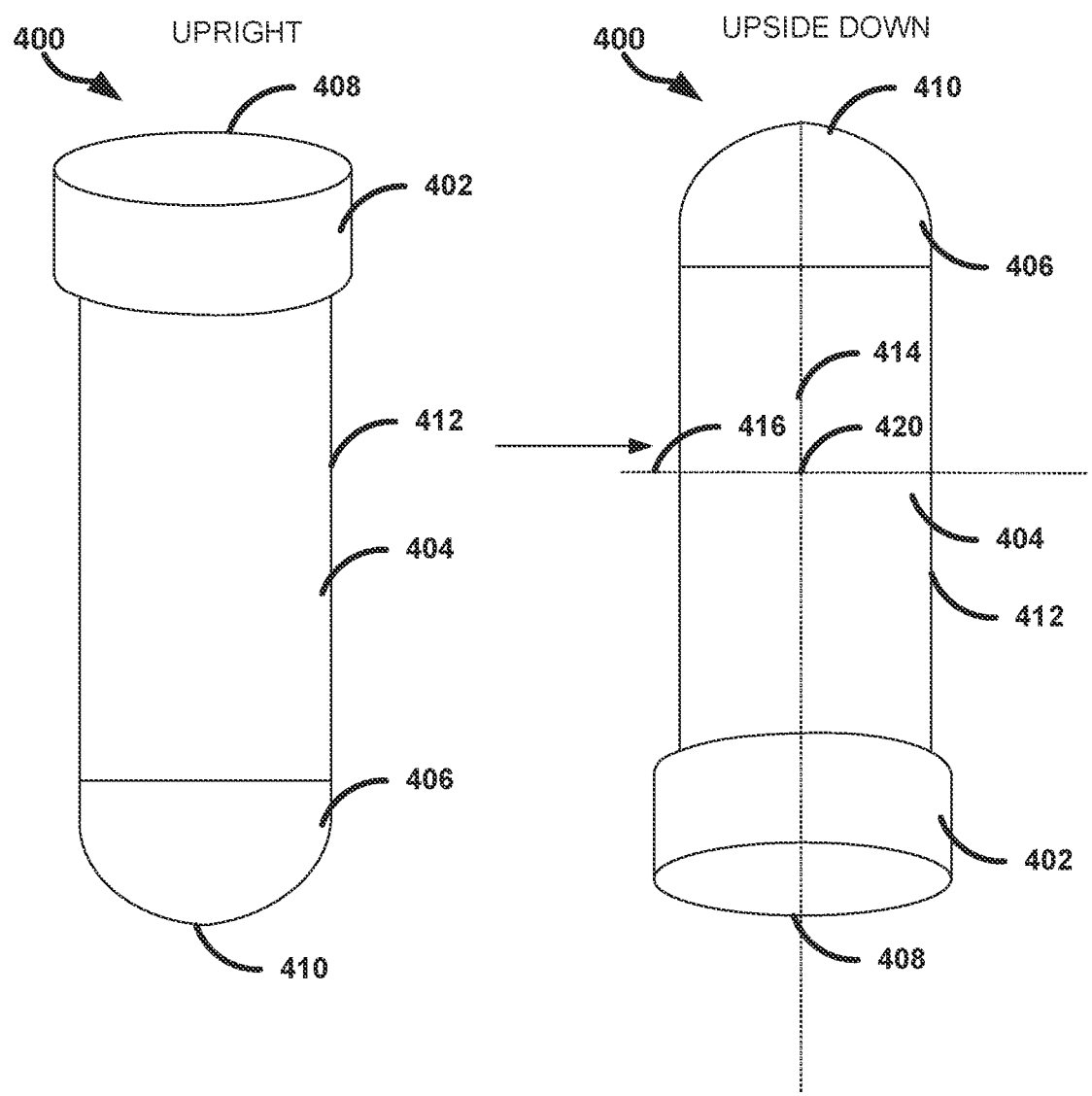
FIG. 4 illustrates, by way of example, a diagram of an embodiment of a full inversion of a tube (sometimes called a container or vial).

FIG. 4 illustrates, by way of example, a diagram of an embodiment of a full inversion of a tube 400 (sometimes called a container or vial). The full inversion includes the vial upright (left side of diagram) and upside down (right side of diagram). The tube 400 as illustrated includes a cap 402 and a tube body portion 404. The tube 400 can optionally include a material 406 therein. The material 406 can include a reagent, such as can include a pro-coagulant, an anti-coagulant, or a composition that alters or reacts with a sample in the tube 400.

Often, the cap 402 is colored, with different colors used for different tests. These different tests and colors can include: a yellow or yellow-black cap 402; a coagulation tube that includes a light blue cap 402; a routine coagulation assay that includes a light blue cap 402; a non-additive tube can include a red cap 402; a serum separator tube (SST) can include a red-gray or gold cap 402 with a gel separator and clot activator material 406; a tube with sodium heparin (anti-coagulant) can include a dark green cap 402; a plasma separator tube (PSI) can include a light green cap 402 and include a lithium heparin anticoagulant and a gel separator material 406; a tube with an ethylenediaminetetraacetic acid (EDTA) material 406 can include a lavender cap 402; a tube with an acid-citrate-dextrose (ACD) A (ACDA) or ACDB material 406 can include a pale yellow cap 402; and a tube with oxalate or fluoride material 406 can include a light gray cap 402. If there is a concern regarding contamination by tissue fluids or thromboplastins, then one may draw a non-additive tube first, and then use the light blue capped tube.

Tubes with such material 406 can include inversion requirements. A tube 400 that is not sufficiently mixed can cause a sample to fail testing, thus causing a re-sample, a mis-diagnosis, or the like. This costs a lot of unnecessary money, time, and resources.

What is considered sufficiently mixed can vary depending on the type of test to be performed. The type of test to be performed (as previously discussed) can be indicated by the color of the cap 402. For example, some tests may require no inversions, such as if the tube 400 includes no material 406 therein. In another example, a tube with a material 406 in it may not require mixing. For example an SPS vial (yellow cap 402) can be required to be inverted 8-10 times, a vial with a dark-blue cap 402 can have no inversion requirement, a vial with a blue cap 402 can be required to be inverted 3-4 times, a vial with a red or orange cap 402 (including a clot activator material 406) can be required to be inverted 5 times, a vial with a gold cap 402 can be required to be inverted 5 times, and a vial with a green, lavender, dark blue (with EDTA material 406), black, gray, or yellow can be required to be inverted 8-10 times.

Figure 5:
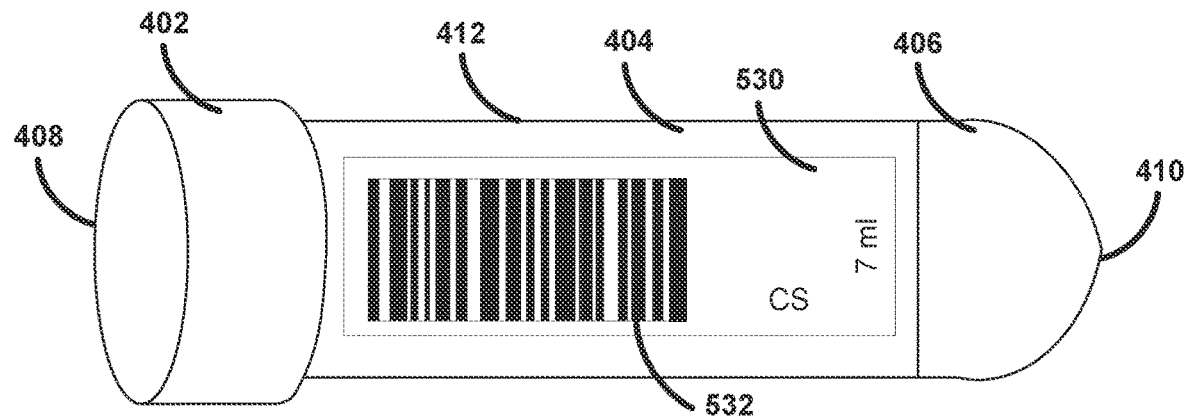
FIG. 5 illustrates, by way of example, a diagram of an embodiment of a tube with a first label.

FIG. 5 illustrates, by way of example, a diagram of an embodiment of a tube 500 with a first label 530. The first label 530 includes a bar code 532. The bar code 532, when decoded provides information including a patient name, a date and time corresponding to the blood or other specimen draw, and a patient identification that uniquely identifies the patient. Other codes, other than bar codes are possible. For example, a quick response (QR) code, a radio frequency (RF) tag, or the like can be used in place of the bar code label.

Figure 6:
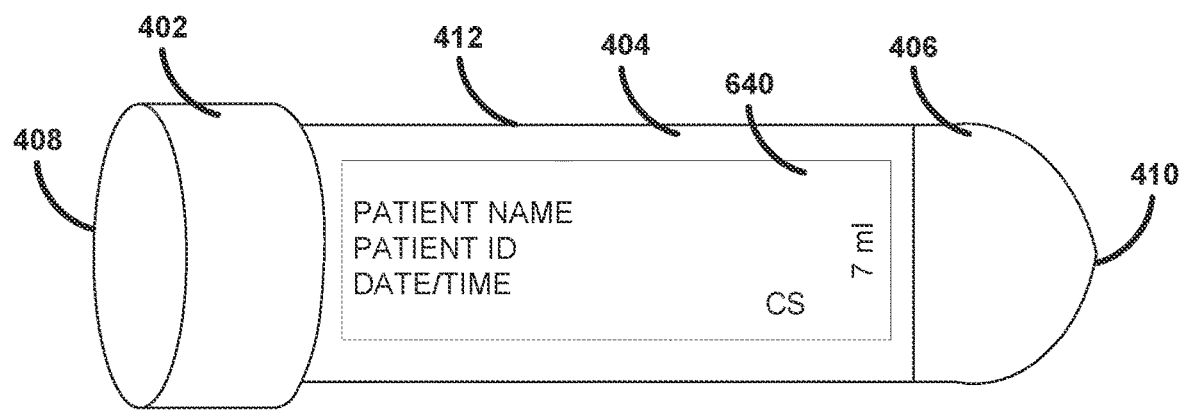
FIG. 6 illustrates, by way of example, a diagram of an embodiment of a tube with a second label.

FIG. 6 illustrates, by way of example, a diagram of an embodiment of a tube 600 with a second label 640. The second label 640 includes text identifying the patient name, the date and time corresponding to the sample collection, and a patient identification that uniquely identifies the patient. Either of the labels 530, 640 can include a phlebotomist's initials.

Figure 7:
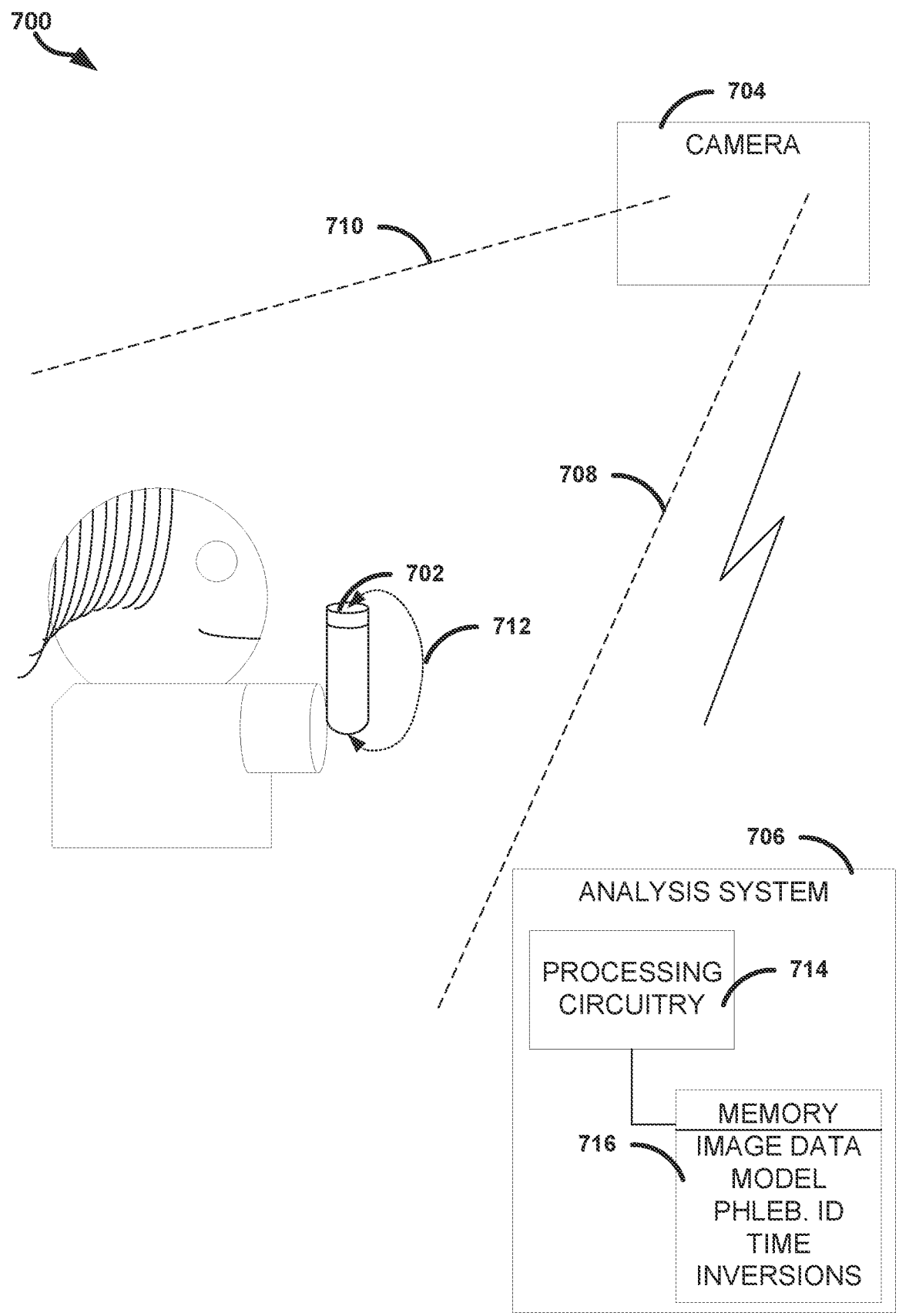
FIG. 7 illustrates, by way of example, a diagram of an embodiment of a system for determining a number of inversions of a sample collection tube.

FIG. 7 illustrates, by way of example, a diagram of an embodiment of a system 700 for determining a number of inversions of a sample collection tube 702. Instead of including the circuitry external to and on the tube as in FIGS. 1, 2A, 2B, the system 700 determines inversions 712 based on object recognition or feature tracking based on image data from a camera 704. The system 700 includes a sample collection tube 702 in a field of view (indicated by dashed lines 708, 710) of a camera 704. The camera 704 generates image data (e.g., grayscale, red, green, blue (RGB), or the like) of a scene in the field of view. The camera 704 can be coupled (wired or wirelessly) to an analysis system 706.

The analysis system 706 can analyze the image data from the camera 704 to determine a number of inversions 712 performed. The analysis system 706 can identify an entity (e.g., phlebotomist) performing the inversions 712 or collecting the samples. The phlebotomist can be identified using a facial recognition technique, or in identifying the initials of the phlebotomist on the label 530, 640. The analysis system 706 can associate the identified phlebotomist or sample with a number of inversions 712 performed.

The analysis system 706 can include processing circuitry 714 and a memory 716. The processing circuitry 714 can implement a model that can produce data that can be used to determine a number of inversions performed by the entity. The model implemented by the processing circuitry 714 can be trained based on images of the vial being upright and upside down or otherwise being handled by the phlebotomist. The images can be labelled upright, upside down, or neither. In some embodiments, rather than use a model, the processing circuitry 714 can use a rule-based technique for inversion detection. Another model can be trained to indicate whether the tube is empty or includes the sample therein. Such a model can be trained based on empty tubes and tubes with samples therein. In general, a tube with a sample therein will be a different color than an empty tube, and the model can distinguish between these colors.

Before the processing circuitry 714 determines whether an image includes a sample vial that is right side up (upright) or upside down, the processing circuitry 714 can first determine whether the tube 702 is present in the image, blood has been drawn into the vial, whether a sufficient amount of biological material is present in the tube 702 and whether any inversions are to be performed.

The processing circuitry 714 can include one or more electric or electronic components configured to perform operations of phlebotomist monitoring or analysis. The electrical or electronic components can include one or more transistors, resistors, capacitors, diodes, inductors, power supplies, switches, logic gates (e.g., AND, OR, XOR, negate, buffer, or the like), processing units (e.g., central processing units (CPUs), application specific integrated circuits (ASICs), field programmable gate arrays (FPGAs), graphics processing units (GPUs), or the like), analog to digital converters, digital to analog converters, regulators, rectifiers, receive or transmit radios, modulators, demodulators, multiplexers, phase locked loops, or the like.

Determining whether the vial is present can be performed using an object recognition technique. Object recognition techniques operate on an image to identify objects in the image. Object recognition can include feature-based detection, genetic techniques, or the like. The feature-based detection can include determining whether an object feature is present in an image. The feature can include a surface patch, a corner, other edge, or the like. Examples of feature-based techniques include interpretation trees, hypothesize and test, alignment, Hough transform, invariance techniques, geometric hashing, scale-invariant feature transform, speeded up robust features (SURF), among others.

For a model-based approach, images can be labelled as "upright", "upside down", or the like, depending on whether a sample collection vial is right side up (upright) or inverted (upside down). The labelled images can be fed to a model that can learn, using a machine learning (ML) technique, parameters that configure the model to classify a given image as corresponding to right side up (upright) or upside down. The ML technique can, based on the training, operate on additional images to determine whether each image corresponds to upright, and then upside down (or vice versa) and determine the number of times a substantially full inversion has occurred.

Features of the tube 400 (see FIG. 4) can include a curvature 408 of the cap 402, an edge 412 between the cap 402 and a bottom of the tube 400, a color of the cap 402, a color of the body portion 404, a curvature of the bottom 410, or the like. In the upright position, the cap 402 is above the bottom 410, and the edge 412 is vertical. In the upside-down position, the bottom 410 is above the cap 402 and the edge 412 is vertical. The trained model can distinguish between these two states.

Determining whether there is sufficient biological material in the tube 702 can include identifying, when the tube 702 is either right side up or upside down, how high on the sidewalls of the tube 702 the biological material covers. The processing circuitry 714 can compare the extent of the biological material to a marking on the tube 702 or determine an extent of the biological material in the tube relative to the extent of the entire tube (such as by pixel counting or the like). The processing circuitry 714 can thus determine whether there is sufficient volume of biological material in the tube 702 to perform the test. The volume of biological material can be different for different tests. The processing circuitry 714 can determine the type of test based on the color of the cap, information on the label or inferred from the label, or the like.

A rule-based inversion detection can use a combination of feature detection, object recognition, and analysis of a sequence in which one or more objects or features are recognized. An object can be detected to be a tube with a sample therein that requires inversion. One or more features of the tube can be identified along with its orientation relative to a midline 414, 416. The lines 414 and 416 on FIG. 4 are examples of midlines. An inversion is detected in response to detecting the same feature on one side of the midline 414, 416 and then on the opposite side of the midline 414, 416. For example, if a feature is on the right side of the midline 414 in the first image and an opposite side of the midline 416 in a second, subsequent image, an inversion counter can be incremented.

The processing circuitry 714 can identify a phlebotomist in the image data. This can be done by identifying initials of the phlebotomist on a label of the blood collection tube, using a facial recognition technique, or decoding information of a bar code on the label. A phlebotomist identification can be associated with the number of counted inversions in the memory 716.

The processing circuitry 714 can identify a time at which the sample was taken. This can be done through associating a time in metadata of the image data from the camera 704, identifying a time in a clock in the image data, identifying the time on a label of the blood collection tube, or decoding information of a bar code on the label.

Figure 8:
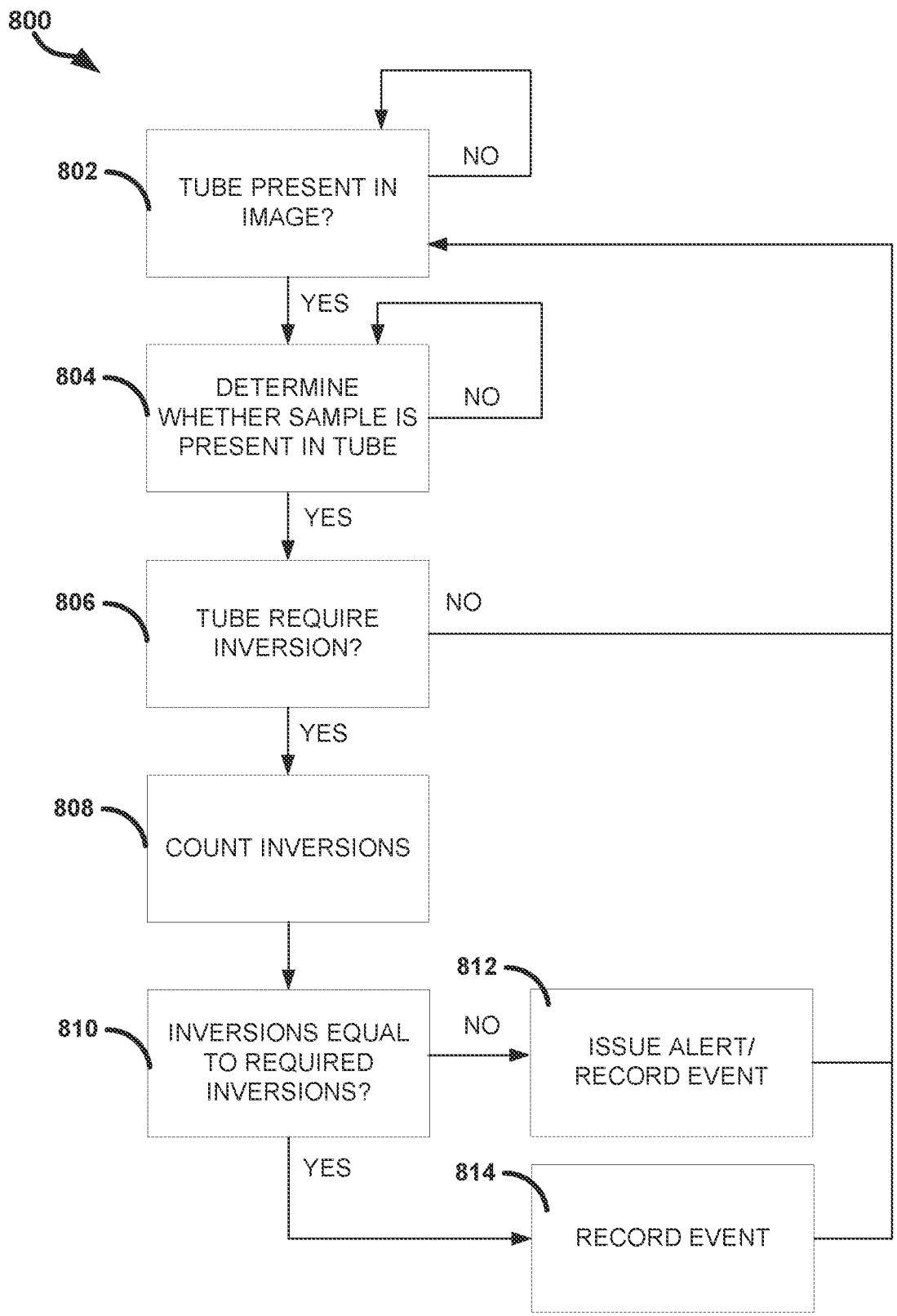
FIG. 8 illustrates, by way of example, a flow diagram of an embodiment of a method for inversion monitoring.

FIG. 8 illustrates, by way of example, a flow diagram of an embodiment of a method 800 for inversion monitoring. The method 800 can be performed, at least in part, by the analysis system 706 (see FIG. 7). The method 800 as illustrated includes determining whether a tube is present in an image (from the camera 704), at operation 802. The operation 802 can include performing object recognition on an image from the camera 704. If a tube is determined to be present in the image, an operation 804 can be performed. If a tube is not present in the image, the operation 802 can be performed again, such as after a specified time delay.

The operation 804 includes determining whether a sample is present in a detected tube. In any given image, one or more tubes can be detected. As multiple tubes may be detected, the analysis system 706 can track multiple tubes simultaneously. If one of the tubes is detected to include a sample (and the tube has not been inverted or before it is determined the tube does not need inverting) it can be determined if the tube requires inversions, at operation 806. If it is determined at operation 804 that the sample is not present, the operation 804 can performed again, such as after a time delay. The operation 804 can include determining whether there is a color change in a body portion 404 of the tube 400. In general, a body portion 404 will get darker when there is blood therein.

At operation 806 it can be determined whether the tube requires inversions. If the tube does not require inversions, the operation 802 can be performed. If the tube does require inversions, an operation 808 can be performed. The operation 806 can include identifying a color of a cap 402 of the tube 400 or whether there is a material 406 in the tube 400. The color of the cap 402 and whether there is material 406 can indicate whether the tube requires inversions and the number of inversions required.

At operation 808 a number of inversions performed on the tube with the sample in it can be counted. At operation 810 it can be determined whether the number of inversions is equal to (or greater than) the required number of inversions. If the inversion count is less than the required number of inversions, an alert can be issued, or the event can be recorded, at operation 812. If the inversion count is greater than (or equal to) the required number of inversions, the event can be recorded. From operations 812, 814 the method 800 can continue at operation 802.

The operation 808 can include object tracking and recognition to determine whether a feature of the tube is detected in opposing quadrants in respective images. Examples of opposing quadrants are (with reference to FIG. 4) (1) above the transverse midline 416 and to the left of the longitudinal midline 414 and below the transverse midline 416 and to the right of the longitudinal midline 414 and (2) below the transverse midline 416 and to the left of the longitudinal midline 414 and above the transverse midline 416 and to the right of the longitudinal midline 414. Thus, if the feature is detected in the quadrant below the transverse midline 416 and to the right of the longitudinal midline 414 in a first image and then detected in the quadrant above the transverse midline 416 and to the left of the longitudinal midline 414 in a subsequent image an inversion count can be incremented. The midlines can remain in their vertical positions and do not rotate with the tube 400 but can move vertically or horizontally to retain an origin 420 at an estimated center of the tube 400. In some embodiments, a feature of the tube 400 below or above the transverse midline 416 can be identified. In response to detecting the feature on above or below the transverse midline 416, a count can be detected. The feature, as previously discussed, can include a curvature of the cap 402, a color of the cap 402, the cap itself 402, a curvature of the bottom edge 410, a mark on the tube, such as a symbol, letter, character or the like on a label of the tube 400, a curvature of an edge of a label on the tube 400, or the like.

Text recognition, sometimes called optical character recognition (OCR), optical word recognition, intelligent character recognition, or intelligent word recognition, is the conversion of an image of characters into machine-encoded characters. In embodiments, text recognition can be used to identify characters in the images from the camera 704. Common operations in text recognition include pre-processing the image (in the region of the characters) by de-skewing, despeckling, binarization, line removal, layout analysis, script recognition (language recognition), character or word isolation, and normalization. There are two basic types of text recognition, matrix matching (sometimes called pattern matching or image correlation) and feature extraction. Matrix matching compares images of a word or character to the captured image to determine a best match. Feature extraction compares features of text extracted from the image, such as closed loops, line direction, and line intersections, to common features of the characters or words. A post-processing operation for text recognition can include constraining the output to a specific lexicon, among other post-processing operations. Using text recognition, a patient name, patient identification, date of sample collection, time of sample collection, phlebotomist name or initials, or a phlebotomist identification can be identified and recorded.

Facial recognition includes techniques for identifying or verifying a person in an image or video. They operate, in general, by comparing selected facial features from an image to facial features or persons of interest in a database. Facial features can include a relative position, size, and shape of the eyes, nose, cheekbones, jaw, or the like. Popular face recognition techniques include principal component analysis using eigenfaces, linear discriminant analysis, elastic bunch graph matching (e.g., using Fisherface), hidden Markov models, the multilinear subspace learning using tensor representation, and dynamic link matching.

Some embodiments of text, object, or facial recognition can be implemented using, at one or more operations, aspects of artificial intelligence (AI), including or processing and inferences performed using machine learning (ML) or neural networks (NNs). AI is a field of technology concerned with developing decision-making systems to perform cognitive tasks that have traditionally required a living actor, such as a person. Neural networks (NNs) are computational structures that are loosely modeled on biological neurons. Generally, NNs encode information (e.g., data or decision making) via weighted connections (e.g., synapses) between nodes (e.g., neurons). Modern NNs are foundational to many AI applications.

Many NNs are represented as matrices of weights that correspond to the modeled connections. NNs operate by accepting data into a set of input neurons that often have many outgoing connections to other neurons. At each traversal between neurons, the corresponding weight modifies the input and is tested against a threshold at the destination neuron. If the weighted value exceeds the threshold, the value is again weighted, or transformed through a nonlinear function, and transmitted to another neuron further down the NN graph—if the threshold is not exceeded then, generally, the value is not transmitted to a down-graph neuron and the synaptic connection remains inactive. The process of weighting and testing continues until an output neuron is reached; the pattern and values of the output neurons constituting the result of the NN processing.

The correct operation of most NNs relies on accurate weights. However, NN designers do not generally know which weights will work for a given application. Instead, a training process (sometimes including ML) is used to arrive at appropriate weights. NN designers typically choose a number of neuron layers or specific connections between layers including circular connection. Instead, a training process generally proceeds by selecting initial weights, which may be specifically or randomly selected. Training data is fed into the NN and results are compared to an objective function that provides an indication of error. The error indication is a measure of how wrong the NN's result is compared to an expected result. This error is then used to correct the weights. Ove iterations, the weights can collectively converge to encode the operational data into the NN. This process may be called an optimization of the objective function (e.g., a cost or loss function), whereby the cost or loss is reduced or even minimized.

A gradient descent technique can be used to perform the objective function optimization. A gradient (e.g., partial derivative) is computed with respect to layer parameters (e.g., aspects of the weight) to provide a direction, and possibly a degree, of correction, but does not result in a single correction to set the weight to "correct" value. That is, via several iterations, the weight can move towards the "correct," or operationally useful, value. In some implementations, the amount, or step size, of movement is fixed (e.g., the same from iteration to iteration). Small step sizes tend to take a long time to converge, whereas large step sizes may oscillate around the correct value or exhibit other undesirable behavior. Variable step sizes may be attempted to provide faster convergence without the downsides of large or small step sizes.

Backpropagation is a technique whereby training data is fed forward through the NN—here "forward" means that the data starts at the input neurons and follows the directed graph of neuron connections until the output neurons are reached—and the objective function is applied backwards through the NN to correct the synapse weights. At each step in the backpropagation process, the result of the previous step is used to correct a weight. Thus, the result of the output neuron correction is applied to a neuron that connects to the output neuron, and so forth until the input neurons are reached. Backpropagation has become a popular technique to train a variety of NNs. Any well-known optimization algorithm for back propagation may be used, such as stochastic gradient descent (SGD), Adam, etc.

Modules, Components and Logic

Certain embodiments are described herein as including logic or a number of components, modules, or mechanisms. Modules may constitute either software modules (e.g., code embodied (1) on a non-transitory machine-readable medium or (2) in a transmission signal) or hardware-implemented modules. A hardware-implemented module is tangible unit capable of performing certain operations and may be configured or arranged in a certain manner. In example embodiments, one or more computer systems (e.g., a standalone, client or server computer system) or one or more processors may be configured by software (e.g., an application or application portion) as a hardware-implemented module that operates to perform certain operations as described herein.

In various embodiments, a hardware-implemented module may be implemented mechanically or electronically. For example, a hardware-implemented module may comprise dedicated circuitry or logic that is permanently configured (e.g., as a special-purpose processor, such as a field programmable gate array (FPGA) or an application-specific integrated circuit (ASIC)) to perform certain operations. A hardware-implemented module may also comprise programmable logic or circuitry (e.g., as encompassed within a general-purpose processor or other programmable processor) that is temporarily configured by software to perform certain operations. It will be appreciated that the decision to implement a hardware-implemented module mechanically, in dedicated and permanently configured circuitry, or in temporarily configured circuitry (e.g., configured by software) may be driven by cost and time considerations.

Accordingly, the term "hardware-implemented module" should be understood to encompass a tangible entity, be that an entity that is physically constructed, permanently configured (e.g., hardwired) or temporarily or transitorily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure a processor, for example, to constitute a particular hardware-implemented module at one instance of time and to constitute a different hardware-implemented module at a different instance of time.

Hardware-implemented modules may provide information to, and receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and store the output of that operation in a memory device to which it is communicatively coupled. A further hardware-implemented module may then, at a later time, access the memory device to retrieve and process the stored output. Hardware implemented modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or processors or processor-implemented modules. The performance of certain of the operations may be distributed among the one or more processors, not only residing within a single machine, but deployed across a number of machines, in some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., Application Program Interfaces (APIs).)

Electronic Apparatus and System

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program may be written in any form of programming language, including compiled or interpreted languages, and it may be deployed in any form, including as a stand-alone program or as a module, subroutine, or other unit suitable for use in a computing environment. A computer program may be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations may also be performed by, and apparatus of example embodiments may be implemented as, special purpose logic circuitry, e.g., a field programmable gate array (FPGA) or an application-specific integrated circuit (ASIC).

The computing system may include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Example Machine Architecture and Machine-Readable Medium (e.g., Storage Device)

Figure 9:
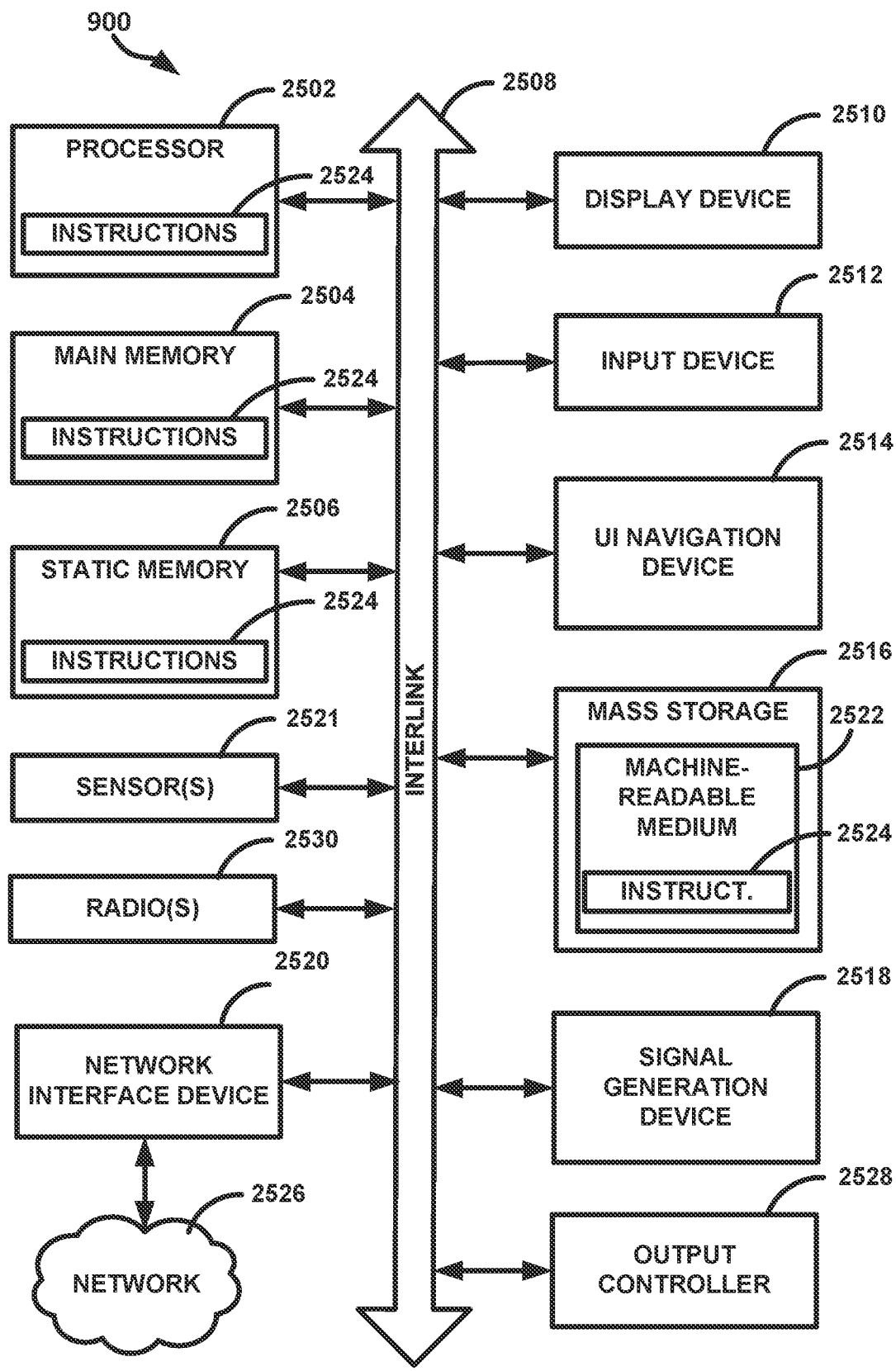
FIG. 9 illustrates, by way of example, a block diagram of an embodiment of a machine in the example form of a computer system within which instructions, for causing the machine to perform any one or more of the methodologies discussed herein, may be executed.

FIG. 9 illustrates, by way of example, a block diagram of an embodiment of a machine in the example form of a computer system 900 within which instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 900 includes a processor 2502 (e.g., processing circuitry, such as can include a central processing unit (CPU), a graphics processing unit (GPU), field programmable gate array (FPGA), other circuitry, such as one or more transistors, resistors, capacitors, inductors, diodes, regulators, switches, multiplexers, power devices, logic gates (e.g., AND, OR, XOR, negate, etc.), buffers, memory devices, or the like, or a combination thereof), a main memory 2504 and a static memory 2506, which communicate with each other via a bus 2508. The computer system 800 may further include a video display unit 2510 (e.g., a liquid crystal display (LCD) or a cathode ray tube (CRT)). The computer system 900 also includes an alphanumeric input device 2512 (e.g., a keyboard), a user interface (UI) navigation device 2514 (e.g., a mouse), a disk drive unit 2516, a signal generation device 2518 (e.g., a speaker), a network interface device 2520, and radios 2530 such as Bluetooth, WWAN, WLAN, and NFC, permitting the application of security controls on such protocols.

Machine-Readable Medium

The disk drive unit 2516 includes a machine-readable medium 2522 on which is stored one or more sets of instructions and data structures (e.g., software) 2524 embodying or utilized by any one or more of the methodologies or functions described herein. The instructions 2524 may also reside, completely or at least partially, within the main memory 2504 and/or within the processor 2502 during execution thereof by the computer system 900, the main memory 2504 and the processor 2502 also constituting machine-readable media.

While the machine-readable medium 2522 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

Transmission Medium

The instructions 2524 may further be transmitted or received over a communications network 2526 using a transmission medium. The instructions 2524 may be transmitted using the network interface device 2520 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

Thus, as described above, the present technology provides a number of benefits. The most direct benefit is an opportunity to improve compliance with blood mixing requirements, as phlebotomists' efforts to reliably mix the blood specimen will be made more measurable. Furthermore, with improved compliance for mixing, time will be saved that is now spent by laboratory personnel attempting to visualize clots within anti-coagulated specimens and preventing their introduction into today's blood analyzers. Furthermore, by improving the mixing, fewer suboptimal specimens will be analyzed by the laboratory, and many negative ramifications may be avoided, such as compromised laboratory instruments, delayed or incorrect diagnoses, increased costs of follow-up patient investigation and associated patient risks.

The embodiments and examples set forth herein are presented to best explain the present technology and its practical application and to thereby enable those skilled in the art to make and utilize the technology. Those skilled in the art, however, will recognize that the foregoing description and examples have been presented for the purpose of illustration and example only. Other variations and modifications of the present technology will be apparent to those of skill in the art, and it is the intent of the appended claims that such variations and modifications be covered.

The description as set forth is not intended to be exhaustive or to limit the scope of the technology. Many modifications and variations are possible in light of the above teaching without departing from the scope of the following claims. It is contemplated that the use of the present technology can involve components having different characteristics. It is intended that the scope of the present technology be defined by the claims appended hereto, giving full cognizance to equivalents in all respects.

I claim:

1. A system comprising:
a camera to capture image data;
an analysis system comprising processing circuitry and a memory, the memory including (i) data indicating a number of inversions required to be performed on a blood collection tube and (ii) instructions that when executed by the processing circuitry, cause the processing circuitry to perform operations for inversion monitoring, the operations comprising:
identifying, using object recognition, whether a blood collection tube is present in the image data;
in response to identifying the blood collection tube is present in the field of view of the camera based on the image data, identifying whether the blood collection tube includes blood therein;
after identifying the blood is present in the blood collection tube, counting, based on the image data and using a computer model trained to distinguish between an upright state of the blood collection tube and an upside down state of the blood collection tube, a number of inversions performed on the blood collection tube; and
in response to determining the number of inversions performed is less than the required number of inversions, issuing, by communications circuitry, an alert indicating that insufficient inversions were performed.

2. The system of claim 1, wherein identifying whether a blood collection tube is present in the image data includes comparing a feature identified in the image data to features of blood collection tubes in the memory.

3. The system of claim 1, wherein identifying whether the blood collection tube includes blood therein includes determining whether a body portion of the blood collection tube has changed color in a series of images.

4. The system of claim 1, wherein the operations further comprise identifying a number of inversions required to be performed on the blood collection container.

5. The system of claim 4, wherein identifying the number of inversions required includes identifying a color of the cap of the blood collection container and looking up the number of inversions associated with the identified color in the memory.

6. The system of claim 5, wherein identifying the number of inversions required includes identifying whether a material is present in a body portion of the blood collection container.

7. The system of claim 1, wherein counting the number of inversions performed on the blood collection tube includes identifying a first feature of the blood collection tube on a cap of the blood collection tube and a second feature on an end portion of the blood collection tube opposing the cap, and for each inversion, determining that pixels corresponding to the first feature are vertically displaced from the second feature in a first direction and then vertically displaced from the second feature in a second, opposite direction in image data corresponding to a subsequent image.

8. The system of claim 1, wherein counting the number of inversions performed on the blood collection tube includes identifying in a quadrant of a logical grid in which a feature is detected and then identifying the feature in an opposing quadrant in image data of a subsequent image, the logical grid non-rotatable and formed at a center of the blood container.

9. The system of claim 1, wherein the model is trained based on images of blood collection tubes labelled upright and upside down and counting the number of inversions performed on the blood collection tube includes detecting in image data of subsequent images the blood collection container is upright and the blood collection container is upside down, respectively.

10. The system of claim 1, wherein the operations further comprise identifying and recording, in the memory, information on a label of the blood collection tube including identifying initials of the phlebotomist and recording a phlebotomist identification associated with the phlebotomist along with the counted number of inversions for each blood collection tube in the memory.

11. The system of claim 1, wherein the operations further comprise using a facial recognition technique to identify a phlebotomist in the image data and recording a phlebotomist identification associated with the phlebotomist along with the counted number of inversions for each blood collection tube in the memory.

12. The system of claim 1, wherein the operations further comprise determining, based on the image data, whether there is a sufficient volume of blood in the blood collection tube to perform a specified test.

13. A non-transitory machine-readable medium including instructions that, when executed by a machine, cause the machine to perform operations for inversion counting and monitoring, the operations comprising:
identifying, using object recognition, whether a blood collection tube is present in image data from a camera situated to capture a series of images of a phlebotomist collecting a sample;
in response to identifying the blood collection tube is present in the field of view of the camera based on the image data, identifying whether the blood collection tube includes blood therein;
after identifying the blood is present in the blood collection tube, counting, based on the image data and using a model trained to distinguish between an upright state of the blood collection tube and an upside down state of the blood collection tube, a number of inversions performed on the blood collection tube; and
in response to determining the number of inversions performed is less than a required number of inversions, issuing an alert indicating that insufficient inversions were performed.

14. The non-transitory machine-readable medium of claim 13, wherein identifying whether the blood collection tube is present in the image data includes comparing a feature identified in the image data to features of blood collection tubes in a memory.

15. The non-transitory machine-readable medium of claim 13, wherein identifying whether the blood collection tube includes blood therein includes determining whether a body portion of the blood collection tube has changed color in the image data.

16. The non-transitory machine-readable medium of claim 13, wherein the operations further comprise identifying a number of inversions required to be performed on the blood collection container.

17. The non-transitory machine-readable medium of claim 16, wherein identifying the number of inversions required includes identifying a color of a cap of the blood collection container and looking up the number of inversions associated with the identified color in the memory.

18. The non-transitory machine-readable medium of claim 17, wherein identifying the number of inversions required includes identifying whether a material is present in a body portion of the blood collection container.

19. A method for phlebotomist monitoring, the method comprising:

identifying, by object recognition implemented by processing circuitry, whether a blood collection tube is present in image data from a camera situated to capture images of a phlebotomist collecting a sample;

in response to identifying the blood collection tube is present in the field of view of the camera based on the image data, identifying, by the processing circuitry, whether the blood collection tube includes blood therein;

after identifying the blood is present in the blood collection tube, counting, based on the image data and by a computer model trained to identify when the blood collection tube is in an upright state and when the blood collection tube is in an upside down state, a number of inversions performed on the blood collection tube; and in response to determining the number of inversions performed is less than a required number of inversions, issuing, by communications circuitry, an alert indicating that insufficient inversions were performed.

20. The method of claim 19, wherein counting the number of inversions performed on the blood collection tube includes identifying a first feature of the blood collection tube on a cap of the blood collection tube and a second feature on an end portion of the blood collection tube opposing the cap, and for each inversion, determining that pixels corresponding to the first feature are vertically displaced from the second feature in a first direction and then vertically displace from the second feature in a second, opposite direction in image data corresponding to a subsequent image.

* * * * *